US011457829B2

(12) United States Patent
Tvedt et al.

(10) Patent No.: US 11,457,829 B2
(45) Date of Patent: Oct. 4, 2022

(54) SENSOR ASSEMBLY

(71) Applicant: SINTEF TTO AS, Trondheim (NO)

(72) Inventors: Lars Geir Whist Tvedt, Oslo (NO); Joar Martin Ostby, Oslo (NO); Thomas Glott, Snaroya (NO); Ingelin Clausen, Oslo (NO)

(73) Assignee: SINTEF TTO AS, Trondheim (NO)

( * ) Notice: Subject to any disclaimer, the term of this patent is extended or adjusted under 35 U.S.C. 154(b) by 332 days.

(21) Appl. No.: 15/771,252

(22) PCT Filed: Oct. 27, 2016

(86) PCT No.: PCT/EP2016/075990
§ 371 (c)(1),
(2) Date: Apr. 26, 2018

(87) PCT Pub. No.: WO2017/072261
PCT Pub. Date: May 4, 2017

(65) Prior Publication Data
US 2018/0310848 A1 Nov. 1, 2018

(30) Foreign Application Priority Data
Oct. 29, 2015 (EP) .................................... 15192057

(51) Int. Cl.
*A61B 5/03* (2006.01)
*A61B 5/00* (2006.01)
(Continued)

(52) U.S. Cl.
CPC ............... *A61B 5/036* (2013.01); *A61B 5/03* (2013.01); *A61B 5/205* (2013.01); *A61B 5/6885* (2013.01);
(Continued)

(58) Field of Classification Search
None
See application file for complete search history.

(56) References Cited

U.S. PATENT DOCUMENTS 3,724,274 A  4/1973 Millar
4,274,423 A  6/1981 Mizuno et al.
(Continued)

FOREIGN PATENT DOCUMENTS

CA  2174897 A1  3/1997
CN  104817053 A  8/2015
(Continued)

OTHER PUBLICATIONS

Machine translation of JP2000292293A (Year: 2000).*
(Continued)

*Primary Examiner* — Sean P Dougherty
*Assistant Examiner* — Benjamin S Melhus
(74) *Attorney, Agent, or Firm* — Cowan, Liebowitz & Latman, P.C.; Mark Montague

(57) ABSTRACT

A sensor assembly for in-vivo monitoring of a body fluid or tissue (F) comprises: a pressure sensor element, comprising a micro-electromechanical system (MEMS) and arranged to detect a pressure of the body fluid or tissue (F) in use; and a shield, which generally surrounds the pressure sensor element such that the pressure sensor element is within an interior volume of the shield, in order to protect and to prevent distortion of the pressure sensor element in use. The pressure sensor element comprises a biocompatible thin film layer, for resisting corrosion and/or fouling of a surface of the pressure sensor element by the body fluid or tissue (F) or biological matter thereof. The pressure sensor element and the shield are in fixed relationship with each other.

24 Claims, 2 Drawing Sheets

(51) Int. Cl.
*A61B 5/20* (2006.01)
*A61M 25/00* (2006.01)

(52) U.S. Cl.
CPC ............... *A61B 2562/0247* (2013.01); *A61M 2025/0002* (2013.01)

(56) References Cited

U.S. PATENT DOCUMENTS

| | | | | |
|---|---|---|---|---|
| 4,456,013 | A * | 6/1984 | De Rossi | A61B 5/02156 600/488 |
| 4,576,181 | A * | 3/1986 | Wallace | A61B 5/0215 600/488 |
| 4,722,348 | A * | 2/1988 | Ligtenberg | A61B 5/0215 73/726 |
| 5,566,680 | A | 10/1996 | Urion et al. | |
| 5,902,248 | A * | 5/1999 | Millar | A61B 8/12 600/485 |
| 6,019,729 | A * | 2/2000 | Itoigawa | A61B 5/0215 600/481 |
| 6,394,986 | B1 * | 5/2002 | Millar | A61B 5/036 600/488 |
| 6,398,738 | B1 * | 6/2002 | Millar | A61B 5/0215 600/486 |
| 7,162,926 | B1 * | 1/2007 | Guziak | A61B 5/0215 73/729.2 |
| 8,140,146 | B2 * | 3/2012 | Kim | A61M 25/0069 600/561 |
| 8,231,537 | B2 * | 7/2012 | Ahmed | A61B 5/02158 600/485 |
| 2003/0028128 | A1 * | 2/2003 | Tenerz | A61M 25/09 600/585 |
| 2005/0187487 | A1 * | 8/2005 | Azizkhan | A61B 5/0215 600/561 |
| 2006/0244177 | A1 * | 11/2006 | Kaneto | A61B 5/03 264/248 |
| 2008/0139959 | A1 * | 6/2008 | Miethke | A61B 5/0031 600/561 |
| 2010/0268123 | A1 * | 10/2010 | Callahan | A61M 25/0662 600/588 |
| 2012/0215133 | A1 * | 8/2012 | Neiman | A61B 5/6852 600/585 |
| 2014/0016719 | A1 * | 1/2014 | Manku | H01Q 7/00 375/295 |
| 2014/0167190 | A1 * | 6/2014 | Hodgson | B81C 3/001 257/415 |
| 2015/0017362 | A1 * | 1/2015 | Matsen | B29C 35/0805 428/35.8 |
| 2015/0021798 | A1 * | 1/2015 | Kimura | B29C 59/022 264/1.27 |
| 2015/0173629 | A1 * | 6/2015 | Corl | A61B 5/02158 600/424 |
| 2015/0223707 | A1 * | 8/2015 | Ludoph | A61B 5/02007 600/487 |
| 2015/0305708 | A1 * | 10/2015 | Stigall | A61B 5/02007 600/467 |
| 2015/0359438 | A1 * | 12/2015 | McCaffrey | A61B 5/02007 600/486 |
| 2016/0081564 | A1 * | 3/2016 | McCaffrey | A61B 5/02141 600/486 |
| 2017/0360369 | A1 * | 12/2017 | Geist | A61B 5/4836 |
| 2018/0010974 | A1 * | 1/2018 | Bueche | A61B 5/145 |

FOREIGN PATENT DOCUMENTS

| | | |
|---|---|---|
| CN | 106028920 A | 10/2016 |
| DE | 38 42 544 A1 | 7/1989 |
| EP | 766946 A2 | 4/1997 |
| EP | 0 907 926 A1 | 2/2003 |
| EP | 3082585 A1 | 10/2016 |
| JP | S54-083488 | 7/1979 |
| JP | 62145780 A | 6/1987 |
| JP | 08247873 A | 9/1996 |
| JP | 10-267775 A | 10/1998 |
| JP | 2000193546 A | 7/2000 |
| JP | 2000-287944 A | 10/2000 |
| JP | 2000-292293 A | 10/2000 |
| JP | 2003065819 A | 3/2003 |
| JP | 2010-029713 A | 2/2010 |
| JP | 2014-214214 A | 11/2014 |
| JP | 2015145801 A | 8/2015 |
| NL | 0263190 A1 * | 4/1988 ........... A61B 5/0215 |
| WO | 2015095280 A1 | 6/2015 |

OTHER PUBLICATIONS

Improved machine translation of JP2000292293A (Year: 2000).*
The above documents were cited the International Search Report of PCT/EP2016/075990 dated Feb. 17, 2017, which is enclosed.
The above references were cited in an JP Office action dated Feb. 24, 2021, which is enclosed, that issued in the corresponding Application No. 2018-521915, and English language copy is attached.

* cited by examiner

SENSOR ASSEMBLY

CROSS REFERENCE TO RELATED APPLICATIONS

This is a U.S. national stage of application No. PCT/EP2016/075990, filed on Oct. 27, 2016. Priority under 35 U.S.C.§ 119(a) and 35 U.S.C.§ 365(b) is claimed from European Patent Application No. 15192057.6, filed on Oct. 29, 2015, the disclosure of which is also incorporated herein by reference.

BACKGROUND OF THE INVENTION

The present invention relates to a sensor assembly for in-vivo monitoring of a body fluid or tissue.

There are many locations within a human or animal body where there are medical benefits in being able to monitor the pressure in fluid or tissue. For example, it can be extremely beneficial in understanding the wellbeing of a patient and understanding the effectiveness of any treatment to the pressure in a patient's cranial fluid, within their bladder, muscle compartments, or within their circulatory system. Because of these benefits, pressure monitoring systems have been developed which can be inserted into the body of a patient to provide pressure readings.

Conventional pressure monitoring systems typically comprise a pressure sensor element at the tip of a catheter. A sealant (comprising, for example, a silicone gel) is provided over the sensor element to provide a pressure transmission medium which also seals the sensor element. A problem with this kind of device is that the fluid being measured tends to leak into the sensor assembly and on to the surface of the sensor element because the sealant is prone to distortion and as a result does not provide a very effective seal. The leakage can damage and even disable the sensor element or its electrical connections/circuit. Furthermore the sensor assembly may produce unreliable pressure readings, in particular due to hysteresis effects caused by the distortable sealant. The hysteresis effects may be exacerbated by leaking fluid. Also, in-use bending of the small, flexible tip can disturb the pressure measurement, introducing unwanted signals in the pressure detection system.

The present invention aims to alleviate at least to some extent one or more of the problems of the prior art.

SUMMARY OF THE INVENTION

The invention is set out in the accompanying claims.

According to an aspect of the invention, there is provided a sensor assembly for in-vivo monitoring of a body fluid or tissue, comprising: a pressure sensor element, comprising a micro-electromechanical system (MEMS) and arranged to detect a pressure of the body fluid or tissue in use; and a shield, which generally surrounds the pressure sensor element such that the pressure sensor element is within an interior volume of the shield, in order to protect and to prevent distortion of the pressure sensor element in use; wherein: the pressure sensor element comprises a biocompatible thin film layer, for resisting corrosion and/or fouling of a surface of the pressure sensor element by the body fluid or tissue or biological matter thereof; and the pressure sensor element and the shield are in fixed relationship with each other.

The invention provides a biocompatible thin film layer which protects a sensor element from potential corrosion and/or fouling by a body fluid or tissue, or biological matter thereof. The sensor element is further protected by a surrounding shield, which is in fixed relationship with the sensor element. The shield is a "stiffener" which has a stiffness that is sufficient to reduce or eliminate stress on the sensor element (and preferably its electrical connections), which may result for example from bending or twisting of the sensor tip. Hence inadvertent mechanical stress in the sensor element, which could lead to undesirable flexure of the pressure-sensitive part of the sensor element and thereby measurement error, can be prevented. Spurious pressure measurements and sensor damage can therefore be avoided.

Thus the biocompatible thin film layer and the shield function together in a synergistic manner to protect the sensor element from corrosion/biofouling and mechanical stress. Advantageously the problematic sealant, required by conventional sensor assemblies as discussed herein above, may be dispensed with. Thus the inventive sensor assembly provides improved accuracy of measurement along with better system reliability and efficiency.

The sensor assembly may comprise a support which supports the pressure sensor element within the interior volume of the shield, the shield having a stiffness which is greater than the stiffness of the support. The support may comprise a portion of a printed circuit board (PCB). Preferably the shield has a stiffness or rigidity, which is sufficient to reduce or eliminate unwanted stress on the pressure sensor element and electrical interconnects between the pressure sensor element and an associated circuit (e.g. of a printed circuit board). The shielding structure may be of greater stiffness than the pressure sensor element.

The pressure sensor element may be fixed relative to the shield by a filler material which fills a cavity in the interior volume of the shield. The shield may comprise a tube. The tube may have an oval cross-section. The pressure sensor element may be positioned adjacent to a first end opening of the tube. Where present, the filler material may be arranged to seal a second end opening of the tube so as to prevent the passage of the body fluid or tissue through the second end opening. The filler material may comprise a cured adhesive. The adhesive may be biocompatible.

The tube may comprise a cut-out which forms an aperture which intersects the first end opening, the pressure sensor element being positioned below the aperture. The cut-out may be inclined relative to the longitudinal axis of the tube. Or, the cut-out may comprise a flat portion and a curved portion such as to be S-shaped in profile. The aperture, which is provided by the cut-out, allows for improved flow and/or circulation of the fluid and improved contact to the tissue being measured. This can help to prevent clogging of the pressure sensor element by tissue or body fluid or biological material thereof, and may prevent the undesirable formation of gas bubbles over the sensor element which could interfere with its function. The shield and aperture can prevent artefacts from the pressure sensor element coming into contact with more dense structures in the body, for example cartilage, bone or fibrous tissue.

The biocompatible thin film layer may have a submicron thickness. The thickness of the layer may be between 20 and 200 nm. The thickness of the layer may be about 30 nm. The layer may comprise a coating. The layer may comprise Al—Ti-oxide. The layer may comprise $Al_2O_3+TiO_2$. Other biocompatible materials may be used for the thin film layer which also can prevent (or at least reduce) corrosion and/or biofouling of the pressure sensor element. Examples of other suitable materials for the thin film layer include, but are not limited to, Diamond-Like-Carbon (DLC), Hydroxyapatite (HA), Silicon Carbide (SiC), and Parylene. The thin film layer may comprise a sandwich structure including a combination of any of the suitable materials.

According to another aspect of the invention, there is provided a sensor system, comprising: a sensor assembly as described herein above; and a catheter hose, configured to connect to the shield of the sensor assembly. Each of the shield and the catheter hose may comprise an oval cross-section, an end of the shield being insertable in an end of the catheter hose, the system comprising a tube or cannula having an oval cross-section for receiving the catheter hose, the pressure sensor element being prevented from rotating about a longitudinal axis of the tube or cannula when the end of the shield is inserted in the end of the catheter hose and the catheter hose is inserted in the tube or cannula. Advantageously the oval shape prevents the pressure sensor element from rotating relative to the cannula, thereby improving the positional and/or directional control of the pressure sensor element during insertion and retraction.

BRIEF DESCRIPTION OF THE DRAWINGS

Embodiments will now be described, by way of example, with reference to the accompanying figures in which.

DETAILED DISCUSSION OF THE EMBODIMENTS

Figure 1:
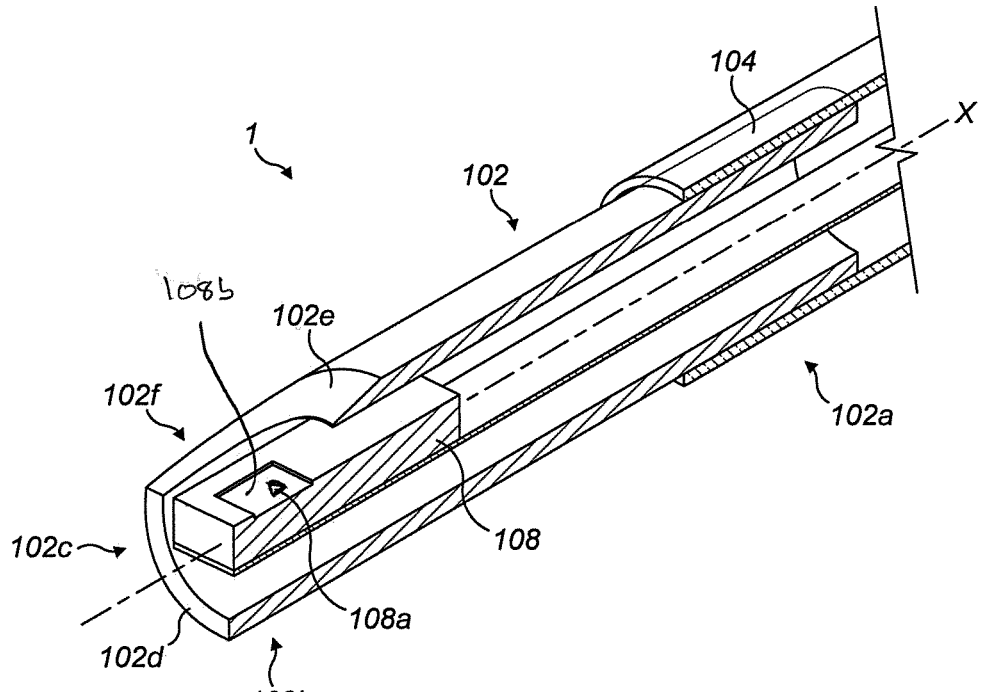
FIG. 1 is a perspective cutaway view of a sensor assembly in accordance with a first embodiment of the invention.
Figure 2:
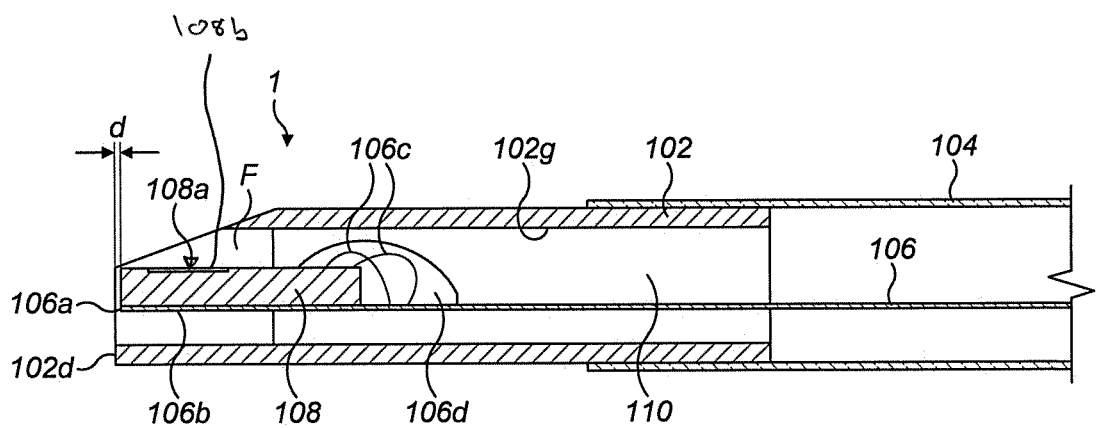
FIG. 2 is a longitudinal sectional view of the sensor assembly of FIG. 1.

Referring to FIGS. 1 and 2, a sensor assembly 1 comprises an elongate stiffener tube 102 having a supported end portion 102a and a free end portion 102b. In this embodiment, the stiffener tube 102 is constructed from AISI 316 stainless steel. The stiffener tube 102 has a length of about 5 mm, an outside diameter of about 1.2 mm, and a wall thickness of about 0.1 mm. (In other embodiments the length may be between about 5 and 10 mm).

The supported end portion 102a is inserted in an end of a catheter hose 104 such that the stiffener tube 102 extends outwardly from the catheter hose 104. An end opening 102c of the stiffener tube 102 is formed by a lip 102d at the extremity of the free end portion 102b. In this exemplary embodiment, an oblique cut-out 102e extends along the free end portion 102b from the lip 102d, in a plane which is inclined relative to the longitudinal axis X of the stiffener tube 102, thereby forming a semi-elliptical aperture 102f which intersects the end opening 102c.

A generally flat, flexible printed circuit board (PCB) 106 lies in a plane which is substantially parallel with the longitudinal axis X of the stiffener tube 102 and extends from the catheter hose 104 through the interior of the stiffener tube 102, such that an end 106a of the flexible PCB 106 is disposed at the end opening 102c. More particularly, the end 106a of the flexible PCB 106 is located within the enclosure of the free end portion 102b at a short distance d (e.g. about 0.1 mm) from the lip 102d. That is, the end 106a does not protrude from the stiffener tube 102.

A pressure sensor element 108 is mounted atop a supporting portion 106b of the flexible PCB 106 which extends to the end 106a of the flexible PCB 106. The pressure sensor element 108 comprises a micro-electromechanical system (MEMS). In this exemplary embodiment the MEMS comprises embedded piezoresistors, pads and conductors (not visible in FIGS. 1 and 2), which are covered by (i.e. disposed below) a membrane or diaphragm 108a. The diaphragm 108a is configured to be deflected by a pressure, which may be applied to the diaphragm 108a by a body fluid or tissue when the sensor assembly 1 is in use. The piezoresistors are configured to detect the deflection of the diaphragm 108a so that the applied pressure can be measured.

A biocompatible thin film layer 108b extends over the diaphragm 108a so as to cover the diaphragm 108a. In this exemplary embodiment the thin film layer 108b comprises $Al_2O_3+TiO_2$. In this embodiment the thin film layer 108b has a thickness of about 30 nm. Alternatively, whatever the material composition of the thin film layer 108b, the thickness may typically be anywhere in the range 20 to 200 nm, or even thicker. Typically the thickness will be a submicron thickness. In use the thin film layer 108b resists (and preferably prevents) corrosion and/or fouling of the surface of the pressure sensor element 108 by a body fluid or tissue or biological matter thereof. Thus the thin film layer 108b protectively covers the pressure-sensing diaphragm 108a, piezoresistors, pads and conductors, in order to avoid damage to the surface of the pressure sensor element 108.

Alternatively the pads and conductors may be disposed on top of (i.e. above) the diaphragm 108a, with the piezoresistors covered by (i.e. disposed below) the diaphragm 108a. In that case the biocompatible thin film layer 108b directly covers the pads and conductors as well as the diaphragm 108a.

The pressure sensor element 108 is electrically connected to the flexible PCB 106 by a plurality of wires 106c, each of which comprises gold in this embodiment. Alternatively the wires may comprise other metals, for example aluminium, as will be apparent to the skilled reader. The ends of the wires 106c are bonded to the pressure sensor element 108 and the flexible PCB 106, at a transition region of the pressure sensor element 108 and the flexible PCB 106. The stiffness of the stiffener tube 102 is greater than the stiffness of the transition region. The ends of the wires 106c are additionally protected by a glob top 106d as will be explained later herein.

An end of the pressure sensor element 108 is aligned with the end 106a of the flexible PCB 106. Accordingly, a portion of the pressure sensor element 108 is disposed adjacent to the end opening 102c and in particular a portion of the pressure sensor element 108 is positioned below the semi-elliptical aperture 102f of the free end portion 102b. No part of the pressure sensor element 108 protrudes beyond the lip 102d or out of the semi-elliptical aperture 102f. That is, the pressure sensor element 108 is contained entirely within the interior volume of the stiffener tube 102. Accordingly, the stiffener tube 102 provides a protective sheath or shield around the pressure sensor element 108. In other words, the pressure sensor element 108 is protectively covered by the stiffener tube 102.

In this embodiment, cured epoxy glue 110 fills a major portion of the interior volume of the stiffener tube 102, and a portion of each of the flexible PCB 106 and pressure sensor element 108 is embedded in the epoxy glue 110, such that the PCB 106 and pressure sensor element 108 are held in substantially fixed relationship with the stiffener tube 102. The diaphragm 108a of the pressure sensor element 108 is free from coverage by the epoxy glue 110, so that in use the diaphragm 108a can be exposed to body fluid or tissue F and deflected by a pressure thereof, in the manner already described.

The sensor assembly 1 can be used to monitor pressure levels of a fluid or tissue F in various parts of a patient's body, in order that an assessment of the patient's condition can be made. For example, the catheter hose 104 and the stiffener tube 102 (containing the pressure sensor element 108) may be inserted, in a conventional manner, through the urinary tract and into the bladder of a patient. The inventive sensor assembly 1 is also well-suited to suprapubic insertion through the abdominal wall of the patient. It will be understood that the sensor assembly 1 may also be inserted into other parts of the body using appropriate techniques. The protective stiffener tube 102 prevents impacts between the pressure sensor element 108 and, for example, body tissue or foreign objects, which might otherwise distort and possibly cause damage to the pressure sensor element 108. As the sensor assembly 1 is established in position in order to monitor the pressure, the body fluid or tissue F to be monitored is able to come into direct contact with the diaphragm 108a of the pressure sensor element 108 through the end opening 102c and also the semi-elliptical aperture 102f, so that accurate pressure measurements can be made. The sensor assembly 1 is connected to an electronic module (not shown in the Figures) which is placed externally of the patient's body and includes a signal processor. Alternatively, the electronic module may be located inside the patient's body, at some determined distance from the pressure sensor element 108 or under the skin, and the signals may be transmitted wirelessly from the module to an external receiver. Pressure readings can be taken from the pressure sensor element 108 and processed by the signal processor over a period of time, for example hours, days, or even years. As the pressure sensing element 108a monitors the pressure, the solid epoxy glue 110 within the interior volume of the stiffener tube 102 provides a seal which prevents fluids from leaking into the catheter hose 104 and the flexible PCB 106.

At the end of the pressure monitoring period the sensor assembly 1 is withdrawn from the patient's body. The stiffener tube 102 protects the pressure sensor element 108 from impact, distortion and damage.

While the exemplary embodiment described herein above includes a tubular sheath for protecting the pressure sensor element, it will be understood by the skilled reader that the shielding structure may take any one of a variety of shapes, as long as the structure provides adequate protection in order to prevent distortion or damage to the pressure sensor element. Preferably the shielding structure (e.g. tubular sheath) has sufficient stiffness or rigidity to reduce or eliminate unwanted stress on the pressure sensor element, and the electrical connection between the pressure sensor element and the PCB, thereby to prevent pressure measurement errors.

It will be further understood that the pressure sensor element may be configured and secured in any one of a variety of ways within the protective structure, and all of these are within the scope of the claimed invention, provided that at least a part of the pressure sensor element (in the above embodiments, the diaphragm) is exposed such that the pressure sensor element can come into contact with the medium to be monitored (e.g. body fluid or tissue, or the like) in order to determine the pressure of the medium.

Figure 3A:
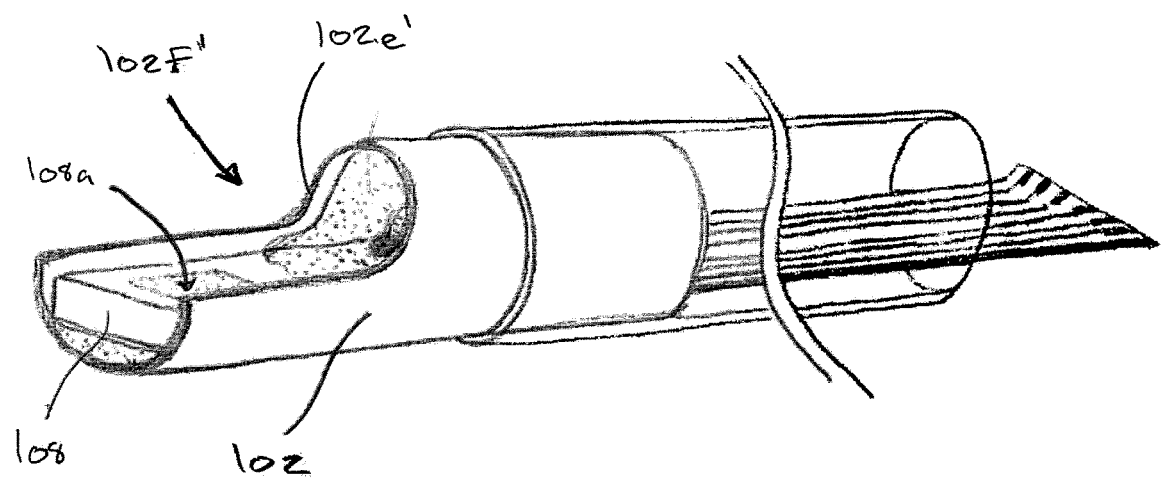
FIGS. 3a and 3b are, respectively, perspective cutaway and longitudinal sectional views of a sensor assembly in accordance with a second embodiment of the invention.
Figure 3B:
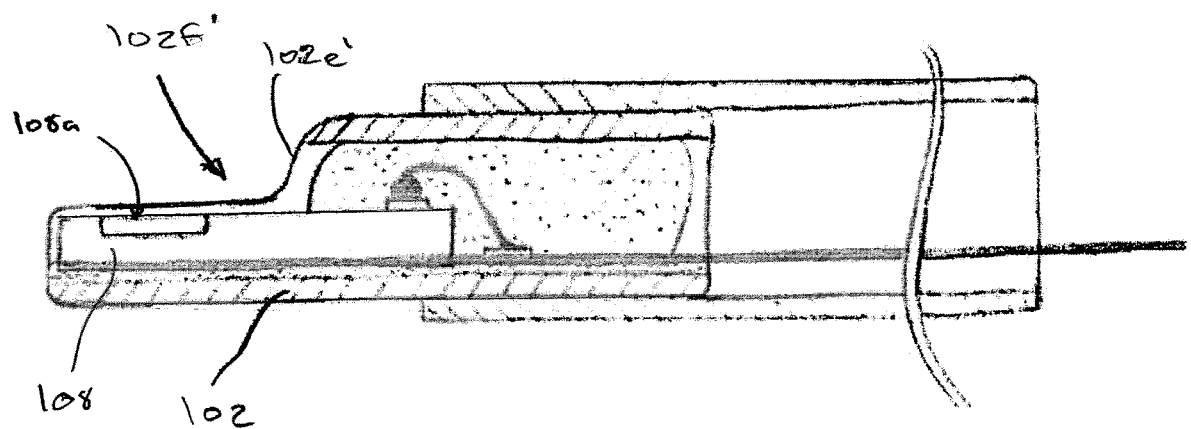

Referring now to FIGS. 3a and 3b, an alternative embodiment of the invention differs from the above-described embodiment with respect to the shape of the cut-out of the stiffener tube 102. In this embodiment, a cut-out 102e' defines an aperture 102f and comprises a flat portion, which extends substantially parallel with the longitudinal axis X of the stiffener tube 102, and a curved portion, such that the cut-out 102e' is generally "S" shaped in profile (as best illustrated in FIG. 3b). This form of cut-out is believed to be particularly effective in preventing the formation of gas bubbles in the aperture 102f over the sensor element 108, which if present could potentially interfere with the function of the sensor element 108.

A sensor assembly 1 according to the invention may be produced according to the following procedure.

The pressure sensor element 108 is mounted to the supporting portion 106b of the flexible PCB 106 such that the end of the pressure sensor element 108 is flush with the end 106a of the flexible PCB 106. The ends of the wires 106c are bonded to the flexible PCB 106 and the pressure sensor element 108 to provide the electrical connection there between. The glob top 106d is provided to ensure that the wires 106c are kept in place during the rest of the assembly process, thereby reducing the possibility of the wires 106c shorting or breaking.

The flexible PCB 106 with the mounted and electrically-connected pressure sensor element 108 is drawn into the free end portion 102b of the stiffening tube 102, until the end 106a of the flexible PCB 106 and the end of the pressure sensor element 108 are at the said distance d from the lip 102d of the free end portion 102b and the pressure sensor element 108 is positioned below the semi-elliptical aperture 102f (or aperture 102f'). The epoxy glue 110 is added to fill the cavities, between the pressure sensor element 108 (only at the end with electrical connections and glob top 106d) and the flexible PCB 106, and the interior wall 102g of the stiffener tube 102. The epoxy glue 110 is allowed to cure in order to fix and hold the flexible PCB 106 and pressure sensor element 108 in position relative to the surrounding stiffener tube 102.

With the flexible PCB 106 and the pressure sensor element 108 fixably attached, the supported end portion 102a of the stiffener tube 102 is drawn into the catheter hose 104 and held thereto in a snug fit. The dimensions of the stiffener tube 102 and catheter hose 104 are selectively matched so as to provide a mechanically stable junction and avoid leakage of fluids between the stiffener tube 102 and the catheter hose 104.

It will be understood that the invention has been described in relation to its preferred embodiments and may be modified in many different ways without departing from the scope of the invention as defined by the accompanying claims.

The stiffener tube 102 may be constructed substantially from AISI 316L low carbon steel. Or, the stiffener tube 102 may be constructed substantially from plastics, which material may be better suited to long term in-vivo applications than metals or metal alloys. Furthermore it will be apparent to the skilled person that other materials, including composite materials, may be appropriate for use in the stiffener tube 102, and all of these are within the scope of the claimed invention.

The wires may be omitted and instead the pressure sensor element 108 electrically connected to the flexible PCB 106 by flip-chip bonding. In this case, during assembly gold bumps are made on bond pads of either the flexible PCB 106 or the pressure sensor element 108. The pressure sensor element 108 is then flipped around and pressed onto the flexible PCB 106 so that the bond pads bond together with the gold bumps, forming a stack of pad-bump-pad.

The sensor element 108 may be additionally fixed by use of underfill epoxy glue. This ensures a mechanical fixation as well as an electrical connection of the pressure sensor element 108.

While in the above-described embodiments the pressure sensor element 108 and the stiffener tube 102 are held in fixed relationship with one another primarily by means of the cured epoxy glue 110, it will be understood that the fixed relationship may be achieved wholly or partially by different means, all of which are within the scope of the claimed invention. For example, some rigid support may be provided to join or connect the pressure sensor element 108 and the stiffener tube 102. Alternatively the flexible PCB 106, the supporting portion 106*b* of which supports the pressure sensor element 108, may be made sufficiently rigid to provide an effective fixed relationship between the pressure sensor element 108 and the stiffener tube 102. In the absence of solid epoxy glue 110, an alternative means of sealing may be provided to prevent fluids from leaking into the catheter hose 104 and the flexible PCB 106.

It will be understood that the cut-out, of the stiffener tube 102, may take a variety of geometrical forms, each of which can provide an aperture over the sensor element, and all of these are within the scope of the claimed invention.

In an embodiment, the sensor assembly 1 includes a catheter and the PCB 106 is replaced by thin (e.g. golden) wires embedded in the catheter wall.

The invention claimed is:

1. A sensor assembly for in-vivo monitoring of a body fluid or tissue, comprising:
   a pressure sensor element located at a distal end region of the assembly, comprising a micro-electro-mechanical system, the pressure sensor element arranged to detect a pressure of the body fluid or tissue in use; and
   wherein a shield with a part of a tubular proximal region thereof surrounds a proximal end region of the pressure sensor element in such a way that the pressure sensor element is enclosed within an interior volume of the tubular proximal region part,
   wherein the pressure sensor element has on a surface thereof a biocompatible thin film layer, for resisting corrosion and/or fouling of the surface of the pressure sensor element by the body fluid or tissue or biological matter of the body fluid or tissue; and
   wherein a curable adhesive filler material causes the pressure sensor element and the shield to be held in a rigid mutually fixed positional relationship, and wherein tubular proximal region part of the shield is filled with the filler material to engage the proximal end region of the pressure sensor element,
   wherein the shield further comprises a distal end region integral with the tubular proximal region, the distal end region being formed as a part cut-out from a tubular distal region blank and exhibiting a distal axial end, and wherein the cut-out part exhibits, as seen in side profile, a flat portion extending parallel to a longitudinal axis of the shield from the distal axial end and continuing into a curved portion being S-shaped in profile to join the tubular proximal region of the shield, the pressure sensor element having its pressure sensitive part positioned at a region of the flat portion and having its distal end face facing said distal axial end of the shield.

2. The sensor assembly according to claim 1, wherein the filler material comprises a biocompatible adhesive.

3. The sensor assembly according to claim 1, wherein the tubular proximal region of the shield exhibits an oval cross-section.

4. The sensor assembly according to claim 1, comprising a flexible printed circuit board which extends through the interior volume of the shield, the pressure sensor element being mounted on a supporting portion of the flexible printed circuit board, wherein a portion of each of the flexible printed circuit board and the pressure sensor element being embedded in the filler material such that the flexible printed circuit board and the pressure sensor element are held in said fixed relationship with the shield when the filler material is cured.

5. The sensor assembly according to claim 1, wherein the filler material inside the tubular proximal region of the shield seals a proximal end opening of the shield so as to prevent the passage of the body fluid or tissue through the proximal end opening.

6. The sensor assembly according to claim 1, wherein the biocompatible thin film layer has a submicron thickness between 20 and 200 nm.

7. The sensor assembly according to claim 1, wherein the biocompatible thin film layer comprises $Al_2O_3+TiO_2$.

8. The sensor assembly according to claim 1, wherein a proximal part of the tubular proximal region of the shield is configured to fit into and engage a distal region of a catheter hose, and wherein the tubular proximal region of the shield and the catheter hose both exhibit an oval cross-section to prevent mutual rotation when engaged.

9. The sensor assembly according to claim 1, wherein a distance between the distal end face of the sensor element and said distal axial end of the shield is 0.1 mm.

10. The sensor assembly according to claim 1, wherein the shield is made from stainless steel.

11. The sensor assembly according to claim 10, wherein the shield has an axial length in the range of 5-10 mm.

12. The sensor assembly according to claim 11, wherein the tubular proximal region of the shield has an outside diameter of approximately 1.2 mm.

13. A sensor assembly for in-vivo monitoring of a body fluid or tissue, comprising:
   a pressure sensor element located at a distal end region of the assembly, comprising a micro-electro-mechanical system, the pressure sensor element arranged to detect a pressure of the body fluid or tissue in use; and
   wherein a shield with a part of a tubular proximal region thereof surrounds a proximal end region of the pressure sensor element in such a way that the pressure sensor element is enclosed within an interior volume of the tubular proximal region part,
   wherein the pressure sensor element has on a surface thereof a biocompatible thin film layer, for resisting corrosion and/or fouling of the surface of the pressure sensor element by the body fluid or tissue or biological matter of the body fluid or tissue; and
   wherein a curable adhesive filler material causes the pressure sensor element and the shield to be held in a rigid mutually fixed positional relationship, and wherein tubular proximal region part of the shield is filled with the filler material to engage the proximal end region of the pressure sensor element,
   wherein the shield further comprises a distal end region integral with the tubular proximal region, the distal end region being formed as a part cut-out from a tubular distal region blank and exhibiting a distal axial end, wherein the cut-out part exhibits one of:
   a) an aperture which intersects a distal axial end of the shield, the pressure sensor element having its pressure sensitive part positioned below the aperture and having a distal end face of the element facing said distal axial end of the shield, the cut-out defining the aperture being inclined relative to a longitudinal axis of the shield, or
   b) as seen in side profile, a flat portion extending parallel to a longitudinal axis of the shield from the distal axial end and continuing into a curved portion being S-shaped in profile to join the tubular proximal region of the shield, the pressure sensor element having its micro-electro-mechanical system positioned at a region of the flat portion and having its distal end face facing said distal axial end of the shield.

14. The sensor assembly according to claim 13, wherein the filler material comprises a biocompatible adhesive.

15. The sensor assembly according to claim 13, wherein the tubular proximal region of the shield exhibits an oval cross-section.

16. The sensor assembly according to claim 13, comprising a flexible printed circuit board which extends through the interior volume of the shield, the pressure sensor element being mounted on a supporting portion of the flexible printed circuit board, wherein a portion of each of the flexible printed circuit board and the pressure sensor element being embedded in the filler material such that the flexible printed circuit board and the pressure sensor element are held in said fixed relationship with the shield when the filler material is cured.

17. The sensor assembly according to claim 13, wherein the filler material inside the tubular proximal region of the shield seals a proximal end opening of the shield so as to prevent the passage of the body fluid or tissue through the proximal end opening.

18. The sensor assembly according to claim 13, wherein the biocompatible thin film layer has a submicron thickness between 20 and 200 nm.

19. The sensor assembly according to claim 13, wherein the biocompatible thin film layer comprises $Al_2O_3+TiO_2$.

20. The sensor assembly according to claim 13, wherein a proximal part of the tubular proximal region of the shield is configured to fit into and engage a distal region of a catheter hose, and wherein the tubular proximal region of the shield and the catheter hose both exhibit an oval cross-section to prevent mutual rotation when engaged.

21. The sensor assembly according to claim 13, wherein a distance between the distal end face of the sensor element and said distal axial end of the shield is 0.1 mm.

22. The sensor assembly according to claim 13, wherein the shield is made from stainless steel.

23. The sensor assembly according to claim 22, wherein the shield has an axial length in the range of 5-10 mm.

24. The sensor assembly according to claim 23, wherein the tubular proximal region of the shield has an outside diameter of approximately 1.2 mm.

\* \* \* \* \*